(12) United States Patent
Marin et al.

(10) Patent No.: US 11,550,151 B2
(45) Date of Patent: Jan. 10, 2023

(54) METHOD OF DETERMINING AN EYE PARAMETER OF A USER OF A DISPLAY DEVICE

(71) Applicant: ESSILOR INTERNATIONAL, Charenton-le-Pont (FR)

(72) Inventors: Gildas Marin, Charenton-le-pont (FR); Martha Hernandez-Castaneda, Charenton-le-pont (FR); Konogan Baranton, Charenton-le-pont (FR); Bruno Fermigier, Charenton-le-pont (FR); Aude Bouchier, Charenton-le-pont (FR); Jean Sahler, Charenton-le-pont (FR)

(73) Assignee: Essilor International, Charenton-le-Pont (FR)

( * ) Notice: Subject to any disclaimer, the term of this patent is extended or adjusted under 35 U.S.C. 154(b) by 0 days.

(21) Appl. No.: 16/345,510

(22) PCT Filed: Oct. 28, 2016

(86) PCT No.: PCT/IB2016/001707
§ 371 (c)(1),
(2) Date: Apr. 26, 2019

(87) PCT Pub. No.: WO2018/078411
PCT Pub. Date: May 3, 2018

(65) Prior Publication Data
US 2019/0310478 A1    Oct. 10, 2019

(51) Int. Cl.
*G02B 27/01* (2006.01)
*H04N 13/344* (2018.01)
(Continued)

(52) U.S. Cl.
CPC ............ *G02B 27/0172* (2013.01); *A61B 3/02* (2013.01); *A61B 3/111* (2013.01); *A61B 3/112* (2013.01);
(Continued)

(58) Field of Classification Search
None
See application file for complete search history.

(56) References Cited

U.S. PATENT DOCUMENTS

| 5,892,540 A | 4/1999 | Kozlowski et al. |
| 2006/0072206 A1* | 4/2006 | Tsuyuki ............... H04N 13/344 359/631 |

(Continued)

FOREIGN PATENT DOCUMENTS

WO    2016/149416 A1    9/2016

OTHER PUBLICATIONS

International Search Report and Written Opinion, dated Aug. 2, 2017, from corresponding PCT application No. PCT/IB2016/001707.

*Primary Examiner* — Andre L Matthews
(74) *Attorney, Agent, or Firm* — Nixon & Vanderhye

(57) ABSTRACT

Disclosed is a method for determining an eye parameter of a user of a display device, the eye parameter relating to a dioptric parameter of an ophthalmic lens to be provided to the user, the method including: a display device providing step, during which a binocular display device is provided to the user,—an image display step, during which an image is displayed to the user when using the display device; a display parameter modifying step, during which at least one parameter of the display device is modified so as to modify the virtual display distance of the perceived image, wherein the display parameter modifying step is repeated until image subjective quality of the perceived image is perceived by the (Continued)

user as optimal; and an eye parameter determining step during which an eye parameter is determined based on the parameter of the display device.

19 Claims, 2 Drawing Sheets

(51) Int. Cl.
    *A61B 3/11*     (2006.01)
    *G06F 3/01*     (2006.01)
    *A61B 3/02*     (2006.01)
    *A61B 3/024*     (2006.01)

(52) U.S. Cl.
    CPC .......... *G06F 3/013* (2013.01); *H04N 13/344* (2018.05); *A61B 3/024* (2013.01)

(56) References Cited

U.S. PATENT DOCUMENTS

| | | |
|---|---|---|
| 2006/0238710 A1 | 10/2006 | Dick et al. |
| 2008/0002262 A1* | 1/2008 | Chirieleison ...... G02B 27/0093 359/630 |
| 2015/0277123 A1* | 10/2015 | Chaum .............. G02B 27/0075 348/62 |
| 2016/0270656 A1 | 9/2016 | Samec et al. |
| 2016/0287153 A1 | 10/2016 | Samec et al. |
| 2017/0000324 A1 | 1/2017 | Samec et al. |
| 2017/0000325 A1 | 1/2017 | Samec et al. |
| 2017/0000326 A1 | 1/2017 | Samec et al. |
| 2017/0000329 A1 | 1/2017 | Samec et al. |
| 2017/0000330 A1 | 1/2017 | Samec et al. |
| 2017/0000331 A1 | 1/2017 | Samec et al. |
| 2017/0000332 A1 | 1/2017 | Samec et al. |
| 2017/0000333 A1 | 1/2017 | Samec et al. |
| 2017/0000334 A1 | 1/2017 | Samec et al. |
| 2017/0000335 A1 | 1/2017 | Samec et al. |
| 2017/0000337 A1 | 1/2017 | Samec et al. |
| 2017/0000340 A1 | 1/2017 | Samec et al. |
| 2017/0000341 A1 | 1/2017 | Samec et al. |
| 2017/0000342 A1 | 1/2017 | Samec et al. |
| 2017/0000343 A1 | 1/2017 | Samec et al. |
| 2017/0000345 A1 | 1/2017 | Samec et al. |
| 2017/0000454 A1 | 1/2017 | Samec et al. |
| 2017/0000683 A1 | 1/2017 | Samec et al. |
| 2017/0001032 A1 | 1/2017 | Samec et al. |
| 2017/0007111 A1 | 1/2017 | Samec et al. |
| 2017/0007115 A1 | 1/2017 | Samec et al. |
| 2017/0007116 A1 | 1/2017 | Samec et al. |
| 2017/0007122 A1 | 1/2017 | Samec et al. |
| 2017/0007123 A1 | 1/2017 | Samec et al. |
| 2017/0007182 A1 | 1/2017 | Samec et al. |
| 2017/0007450 A1 | 1/2017 | Samec et al. |
| 2017/0007799 A1 | 1/2017 | Samec et al. |
| 2017/0007843 A1 | 1/2017 | Samec et al. |
| 2017/0010469 A1 | 1/2017 | Samec et al. |
| 2017/0010470 A1 | 1/2017 | Samec et al. |
| 2017/0017083 A1 | 1/2017 | Samec et al. |
| 2017/0154464 A1* | 6/2017 | Lanier ................ G02B 27/0172 |
| 2017/0171533 A1* | 6/2017 | Benitez ................. G02B 30/27 |

* cited by examiner

METHOD OF DETERMINING AN EYE PARAMETER OF A USER OF A DISPLAY DEVICE

FIELD OF THE INVENTION

The invention relates to a method for determining an eye parameter of a user of a display device, the eye parameter may relate to the interpupillary distance of the user.

BACKGROUND OF THE INVENTION

Usually, a person wishing to have an optical equipment goes to see an eye care practitioner.

The eye care practitioner orders the eyewear equipment at an optical lab by sending an order request to the optical lab. The order request may comprise wearer data, for example the wearer's prescription, fitting data, spectacle frame data, for example the type of spectacle frame the wearer has selected, and lens data, for example the type of optical lens the wearer has selected.

The determination of the wearer's prescription and fitting data may require carrying out complex and time consuming measurements. Such measurements usually require complex and costing material and qualified personnel to be carried out.

The usual methods for determining the eye parameters of the user are usually considered long and complex to implement.

For example, a person wanting to determine his or her Inter-Pupillary distance without the help of a third party may implement a method known as the mirror method.

The person needs a ruler with millimeter units and a mirror. To increase the measuring accuracy, the person is to be in a well-lit area so that he or she can line up the ruler and see the ruler markings. In order to get a good reading, the person needs to stand approximately 20 centimeters from the mirror. A person having viewing issues may need to adapt the distance or may need to use his or her ophthalmic lenses that may affect the measurement.

The person is to hold the ruler right above her or his eyes, straight across his or her eyebrows.

The person should keep her or his head straight and upright to ensure a proper measurement.

It's easier for the person to measure one eye at a time by closing the other eye. For example, the person may start by closing his or her right eye and hold the zero millimeter mark right above the exact center of his or her left pupil.

If the zero mark is not perfectly aligned with the center of the left pupil the whole measurement may be altered.

Without moving his or her head or the ruler at all, the person is to open his or her right eye and find the exact millimeter mark that falls on his or her right pupil.

To ensure an accurate reading the person need to look straight ahead at the mirror.

The millimeters that lines up with the exact center of his or her right pupil corresponds to the Inter-Pupillary distance of the person.

To assure an accurate determination of the Inter-Pupillary distance, the person is to repeat the measurements at least three or four times.

Other Inter-Pupillary distance determining methods exists but are usually as complex to implement or require the presence of an eye care professional.

Therefore, there is a need for a method for determining eye parameters of a person that would not be as complex and long to implement as the prior art methods.

One object of the present invention is to provide such method.

SUMMARY OF THE INVENTION

To this end, the invention proposes a method for determining an eye parameter, for example a geometrical eye parameter, of a user of a display device, the method comprising:
  a display device providing step, during which a binocular display device is provided to the user, the binocular display device is configured to display independently images towards the two eyes of the user,
  an image display step, during which an image is displayed to the user when using the display device,
  a display parameter modifying step, during which at least one parameter of the display device is modified so as to modify the quality of the perceived image,
  wherein the display parameter modifying step is repeated until image subjective quality of the perceived image is perceived as optimal by the user, and
  an eye parameter determining step during which an eye parameter is determined based on the parameter of the display device.

Advantageously, the method of the invention allows the user determining his or her eye parameter using a simple and playful method. The user may further configure the display device or order an optical equipment based on the determined eye parameter.

Furthermore, the method of the invention enables carrying out tests in a more friendly or ecological situation.

According to further embodiments which can be considered alone or in combination:
  the binocular display device is configured to displaying images towards the two eyes of the user having both independent features and common features; and/or
  the subjective quality of the perceived image relates to the subjective distortion of the perceived image; and/or
  the display device comprises a right and left lens through which the user sees the images displayed to the right and left eyes respectively and prior to the display image step the method comprises an image processing step during which the image to be displayed is processed to compensate the optical distortion induced by the lenses through which the user sees the images displayed; and/or
  during the display parameter modifying step the image to be displayed is processed until the subjective distortion of the perceived image is canceled or perceived as optimal by the user; and/or
  the display device comprises moveable lenses through which the user sees the images displayed and during the display parameter modifying step the lenses are moved in a plan perpendicular to the optical axis of said lenses until the subjective distortion of the perceived image is perceived as optimal by the user; and/or
  the image displayed to the user comprises a grid; and/or
  the geometrical eye parameter of the user relates to the interpupillary distance; and/or
  the image displayed to the user comprises an element displayed straight ahead for the user and the subjective quality of the perceived image relates to the visibility of the element in the perceived image by the user; and/or
  the display device comprises a moveable display pupil through which the user sees the images displayed and during the display parameter modifying step the moveable display pupil is moved in a plan perpendicular to the optical axis of the display device so as to determine the extreme vertical or horizontal positions of the display pupil within which the user sees the element in the perceived image, the extreme vertical or horizontal position are used to determine the center of rotation of the eyes of the user and/or size of the pupil of the wearer during the geometrical eye parameter determining step; and/or the display device comprises a light-field lenses array through which the user sees the images displayed and during the display parameter modifying step the image is displayed through each lenses of the light-field lenses array so as to determine the extreme vertical or horizontal position of the lenses within which the user sees the element, the extreme vertical or horizontal position being used to determine the center of rotation of the eyes of the user and/or size of the pupil of the wearer during the geometrical eye parameter determining step.

The invention further relates to a computer program product comprising one or more stored sequences of instructions that are accessible to a processor and which, when executed by the processor, causes the processor to carry out at least the display image step, the display parameter modifying step and the eye parameter determining step of the method according to the invention.

The invention also relates to a computer-readable storage medium having a program recorded thereon; where the program makes the computer execute at least the display image step, the display parameter modifying step and the eye parameter determining step of the method of the invention.

The invention further relates to a device comprising a processor adapted to store one or more sequence of instructions and to carry out at least the display image step, the display parameter modifying step and the eye parameter determining step of the method according to the invention.

The invention further relates to a system for determining an eye parameter of a user of a display device, the system comprising:

display device providing means, configured to provide to a user a binocular display device, the binocular display device being configured to display independently images towards the two eyes of the user, image display means, configured to display an image to the user when using the display device, display parameter modifying means, configured to modify at least one parameter of the display device so as to modify the quality of the perceived image, wherein the display parameter modifying means are further configured to modify the at least one parameter until image subjective quality of the perceived image is perceived by the user as optimal, and eye parameter determining means configured to determine an eye parameter based on the parameter of the display device.

BRIEF DESCRIPTION OF THE DRAWINGS

Embodiments of the invention will now be described, by way of example only, and with reference to the following drawings in which.

DETAILED DESCRIPTION OF PREFERRED EMBODIMENTS

Elements in the figures are illustrated for simplicity and clarity and have not necessarily been drawn to scale. For example, the dimensions of some of the elements in the figure may be exaggerated relative to other elements to help improve the understanding of the embodiments of the present invention.

The invention relates to a method for determining an eye parameter of a user of a display device.

The eye parameter may relate to the interpupillary distance and/or the position of the center of rotation of the eyes and/or the pupil diameter and/or the eye curvature of the user.

In the sense of the invention the interpupillary distance (IPD) is the distance between the center of the pupils of the two eyes of the user.

Figure 1:
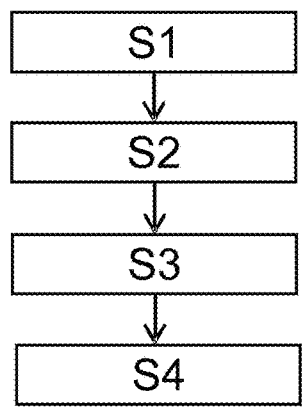
FIG. 1 is a flow chart representing a method for determining an eye parameter of a user of a display device according to the invention.

As illustrated on FIG. 1, the method according to the invention comprises at least:

a display device providing step S1,
an image display step S2,
a display parameter modifying step S3, and
an eye parameter determining step S4.

A binocular display device is provided to the user during the display device providing step S1.

Figure 2:
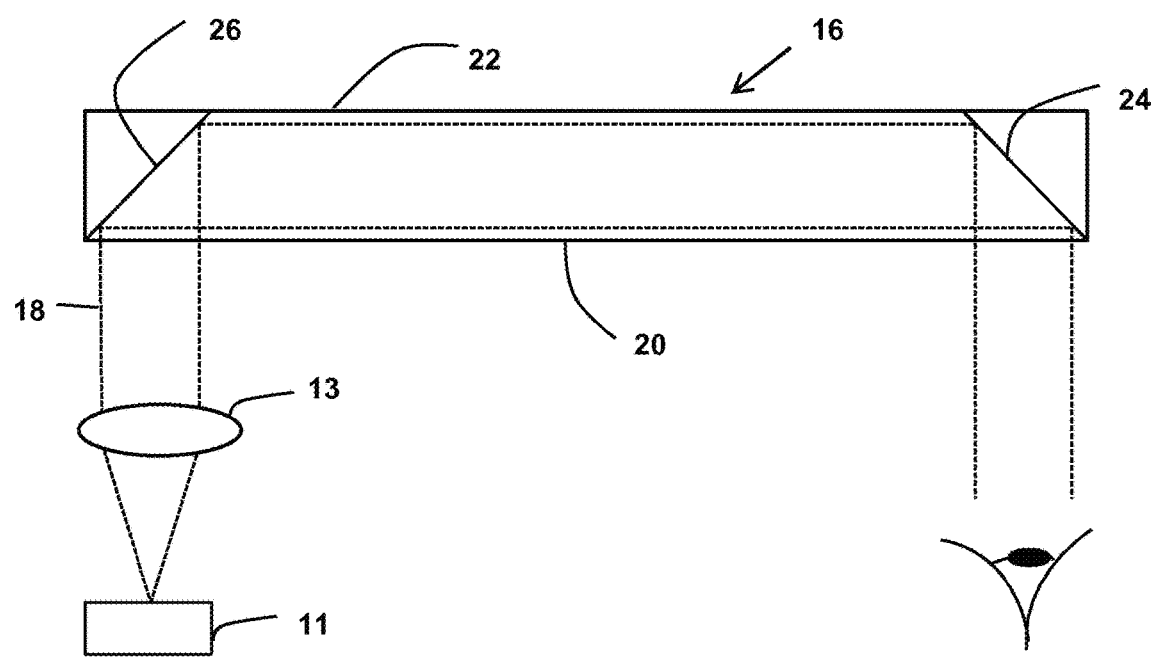

As represented on FIG. 2, the display device according to the invention may preferably comprise a see-through display system, allowing the wearer to see both the virtual image and the real world through it. The see-through display system is able to display graphical images, and an electronic driving system (memory+processor) sends to the display system the image to display. Preferably it is able to display image in different viewing directions. Furthermore, the image to be displayed can be modified.

An example of see-through display system is illustrated on FIG. 2. Such see-trough display system comprises a display source 11, a collimating device 13, and an optical insert 16 constituted by a light-guide optical element 16 (LOE).

The display source 11 can be emissive or not emissive.

It can be directly obtained from either a spatial light modulator (SLM) such as a cathode ray tube (CRT), a liquid crystal display (LCD), an organic light emitting diode array (OLED), liquid crystal on silicon (LCoS) or similar devices, or indirectly, by means of a relay lens or an optical fiber bundle. The display source 11 comprises an array of elements (pixels) imaged to infinity by the collimating device 13, for example a collimating lens.

The light-guide optical element 16 typically includes at least two major surfaces 20 and 22 and edges, at least one partially reflecting surface 24 and an optical element 26 for coupling light thereinto. The output waves 18 from the collimating device 13 enter the light-guide optical element 16 through its lower surface 20. The incoming waves (towards the light-guide optical element 16) are reflected from the surface 26 and trapped in the light-guide optical element 16.

In an embodiment, the see-through display system may comprise a plane light-guide optical element 16 with at least two planes major surfaces 20 and 22. For example, such a light guide optical element 16 may be one of Lumus Company.

In an alternative embodiment, the see-through display system may comprise a curved light-guide optical element 16.

The light-guide may be encapsulated in an optical lens or placed in front of an optical lens.

Figure 3:
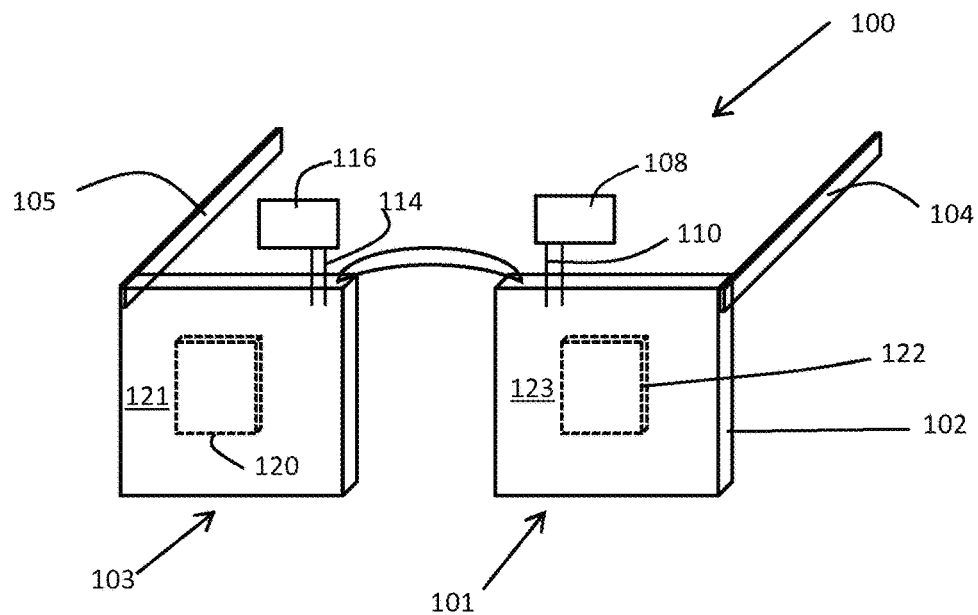
FIGS. 2 and 3 illustrate binocular display devices that may be used in the method of the invention.

The display device is a binocular display device that according to some embodiment of the invention may be head mounted device as represented on FIG. 3.

In this example, the display device comprises a frame. The frame may be similar to a conventional eyeglasses frame and can be worn with a similar comfort level. However, other implementations are possible, such as a face shield which is mounted to the user's head by a helmet, strap, hold by the user himself, or other means, for example VR HMD such as the Rift, the Gear VR or the DK2 from the company Oculus or the Google cardboard.

The frame includes a frame front 102 and temples 104 and 105. The frame front holds a see-through lens 101 for the user's left eye and a see-through lens 103 for the user's right eye. The left and right orientations are from the user's perspective.

The left-side see-through lens 101 includes an optical component 122 such as a beam splitter which mixes an augmented reality image with light from the real-world scene for viewing by the left eye.

The right-side see-through lens 103 includes an optical component 120 such as a beam splitter which mixes an augmented reality image with light from the real-world scene for viewing by the right eye.

A right-side augmented reality emitter 116 is mounted to the frame via an arm 114, and a left-side augmented reality emitter 108 is mounted to the frame via an arm 110.

An electrical power source, for example a battery, provides power to the different elements of the head mounted device.

Appropriate electrical connections can be made via conductive paths in the frame, for instance.

Component 122 and 120 may also include a dimmer that can be an electro active dimmer, such as an electrochromic device, or a liquid crystal dimmer.

This dimmer may be active so as to block light coming from external environment during the image display step S2, allowing the user not to be disturb and only perceive virtual image. This ensures that contrast is maximum.

The binocular display device provided during the display device providing step is configured to display independently images towards the two eyes of the user.

During the image display step S2, an image is displayed to the user when using the display device.

Furthermore, the binocular display device may be configured to display images towards the two eyes of the user having both independent features and common features.

The binocular display device may be configured to display similar features which can be different in some conditions and common in other ones. For example, the display distance can be the same, but the convergence angles of the two images are different.

According to a further example, the distances are different, but convergence angles are the same.

At least one display parameter of the binocular display device is modified during the display parameter modifying step S3 so as to modify the quality of the perceived image.

This can be achieved in different ways: displays generally have an adjustment lens between the eye and the display to compensate for the short distance and return the image to infinity.

The quality of the perceived image may be changed by adjusting the image to be displayed knowing the optical function of the adjustment lenses.

The quality of the perceived image may also be changed by adjusting the position of the adjustment lenses.

For example, according to an embodiment of the invention, the display device comprises moveable lenses through which the user sees the images displayed and during the display parameter modifying step S3 the lenses are moved so as to modify the quality of the perceived image.

Such variation is ideally continuous, but can also be carried in a discrete manner.

The display parameter modifying step s3 is repeated until the subjective quality of the perceived image is perceived by the user as optimal.

The subjective quality of the perceived image may relate to the distortion or the visibility of the perceived image.

The display image and display parameter modifying steps may be implemented in binocular vision. In other words, having the user use both eyes and displaying images to both eyes of the user.

Alternatively, the display image and display parameter modifying steps may be implemented in monocular vision. In other words, having the user use one eye at a time and displaying images to said eye of the user.

According to embodiment of the invention, the subjective quality of the perceived image relates to the subjective distortion of the perceived image.

Indeed, in most head mounted display devices, such as virtual reality helmets, optical lenses for returning the image to infinity are of very short focal length, usually no more than a few centimeters generating important distortions.

Such distortions are generally offset by opposite distortion on images displayed for a better quality of restitution of the virtual images.

For optimal compensation of the distortion it is best to consider the interpupillary distance of the user.

In most current systems the compensation is calculated for eyes centered on the optical center of the lens, the spacing is set at the interpupillary distance of the user in order to compensate optimally distortion at best.

If the user's interpupillary distance does not correspond to the distance between the optical centers of the two lenses a residual distortion appears to the user.

This residual distortion can thus be used to find the optimal position of the optical center of the lenses and thus determining the interpupillary distance of the user.

To determine the interpupillary distance of the user, one can move the lenses to determine the position of the lenses that minimize the subjective distortion of the perceived image.

When the display device is configured for centered compensation, the subjective distortion of the perceived image is minimum when the optical center of each lens is aligned with the pupils of the user.

The distance between the optical center of the lenses therefore provides the interpupillary distance of the user.

According to an embodiment of the invention, the interpupillary distance may be found without moving the lenses by modifying the image to be displayed to compensate the optical distortion induced by the lenses.

Using a ray tracing method, the skilled person may determine the interpupillary distance of the user from the modified image that minimizes the subjective distortion of the perceived image.

According an embodiment of the invention, the image displayed to the user is a grid. Advantageously, using a grid helps the user judge distortion.

For example, one can use a 3D virtual environment in which a grid is virtually fixed in front of the user, so that when the user moves his head, the image of the grid moves behind the lenses of the display system.

The residual distortions then changes dynamically. This condition is particularly suitable for detecting residual distortions.

Indeed, in a static mode the user is to determine whether the grid is deformed without reference mark but the human brain is particularly suitable for offset static deformation and the user may compensate for the distortion.

Whereas with dynamic distortion and especially if the vision is binocular, the human brain cannot compensate. The remaining distortions are perfectly perceptible and position measurement corresponding to the interpupillary distance of the user becomes very sensitive.

Figure 4:
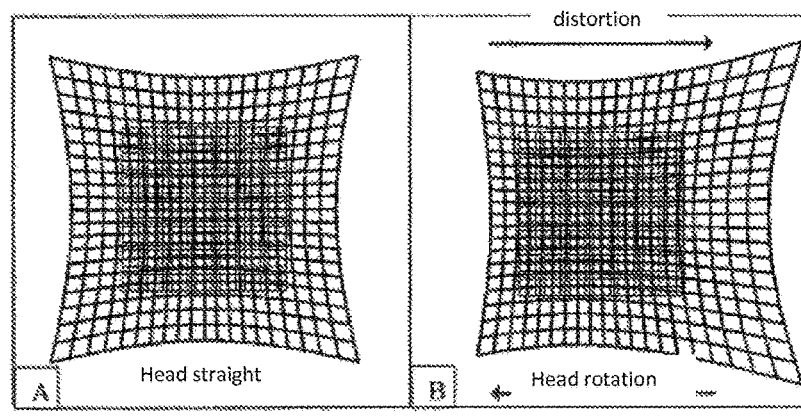
FIGS. 4A and 4B illustrate an embodiment of the invention for measuring the interpupillary distance of the user.

FIG. 4A represents the subjective distortion when the grid and the eye of the user are centered on the optical center of the lenses.

FIG. 4B represents the subjective distortion when the eye of the user or the grid are not centered on the optical center of the lenses. When the user moves his head, the grid moves in front of the lenses and the subjective distortion changes in the direction of the arrows.

The method of the invention may further be used to locate the center of rotation of the eye of the user.

The first step is to locate the center of rotation of the eye of the user in a transverse plane, that is in a plane orthogonal to the optical axis of the display device and the pupil diameter of the user.

Figures 5, 6:
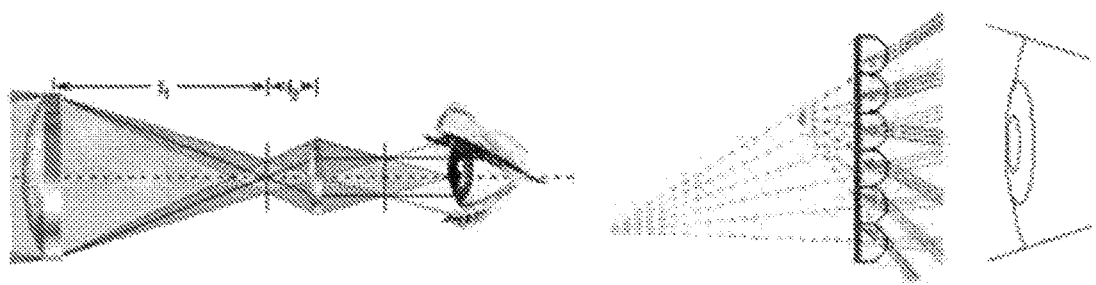
FIG. 5 illustrates a conventional refractive device that may be implemented in a display device.
FIG. 6 illustrates a plenoptic system.

First a virtual image is displayed right in front of the user. The pupil of the user is then shifted, using a conventional refractive device as illustrated on FIG. 5 or by moving the pixel area lit under each micro-lens on a plenoptic system as represented on FIG. 6.

This generates a horizontal or vertical movable light beam, whose diameter is limited by the diameter of the micro-lens where is the active pixel, and this moving beam is perceived by the eye of the user only when it overlap at least partially the pupil of the user.

When the pupil of the user and the exit pupil of the display device don't overlap, the virtual image is hidden. When the pupil of the user and the exit pupil of the display device overlap, even partially, the virtual image is visible for the user.

One may consider the extreme value adjustment or micro-lens positions, X1 and X2, or Y1 and Y2 to which the virtual image appears or disappears for the user.

The average of these two values correspond to the position of the center of rotation of the eye CRE, that is $X_{CRE}=(X1+X2)/2$, and $Y_{CRE}=(Y1+Y2)/2$.

The absolute value of the difference of these two values is the sum of the diameter DPD of the exit pupil of the display device and the diameter DP of the pupil of the user, that is $|X2-X1|=DPD+DP$.

Therefore, knowing the diameter of the exit pupil of the display device, one can determine the diameter of the pupil of the user, $DP=|X2-X1|-DPD$ To determine when the light beam is seen, the user can be asked to report it by pressing a button or equivalent.

In a second step, the radius RE of the eye of the user may be determined, that is to say the distance between the pupil and the center of rotation of the eye of the user.

An eccentric virtual object of a variable angle A is displayed on the edge of the visual field, and possibly shift the $X_{CRE}$ of a value dX in the opposite direction. If the maximum eccentricity of the device is reached, and the virtual image is still visible for the user dX is to be increased.

The offset of the user's pupil is the sum of the rotational movement and the initial offset that is $RE*\sin(A)+X$, with RE the radius of the eye of the user.

When the virtual image disappears, the exit pupil of the device and the pupil of the user do not overlap anymore, the offset corresponds to half the sum of the diameters of the pupils.

So that: $RE*\sin(A)+X=DSP+DP$, providing that $RE=(DSP+DP-X)/\sin(A)$

To measure both eyes, it is possible to make two consecutive monocular measures, or choose objects that the user cannot merge.

The invention has been described above with the aid of embodiments without limitation of the general inventive concept; in particular the mounted sensing device is not limited to a head mounted device.

Many further modifications and variations will suggest themselves to those skilled in the art upon making reference to the foregoing illustrative embodiments, which are given by way of example only and which are not intended to limit the scope of the invention, that being determined solely by the appended claims.

In the claims, the word "comprising" does not exclude other elements or steps, and the indefinite article "a" or "an" does not exclude a plurality. The mere fact that different features are recited in mutually different dependent claims does not indicate that a combination of these features cannot be advantageously used. Any reference signs in the claims should not be construed as limiting the scope of the invention.

The invention claimed is:

1. Method for determining an eye parameter, for example an geometrical eye parameter, of a user of a display device, the method comprising:
 a display device providing step, during which a binocular display device is provided to the user, the binocular display device is configured to display independently images towards the two eyes of the user,
 an image display step, during which an image is displayed to the user when using the display device,
 a display parameter modifying step, during which at least one parameter of the display device is modified so as to modify the distortion or visibility of the perceived image,
  wherein the display parameter modifying step is repeated until image subjective distortion or visibility of the perceived image is perceived as optimal by the user, and
 an eye parameter determining step during which an eye parameter is determined based on the parameter of the display device, wherein the image displayed to the user comprises an element displayed straight ahead for the user and the subjective quality of the perceived image relates to the visibility of the element in the perceived image by the user, and wherein the display device comprises a light-field lenses array through which the user sees the images displayed and during the display parameter modifying step the image is displayed through each lenses of the light-field lenses array so as to determine the extreme vertical or horizontal position of the lenses, the extreme vertical or horizontal position corresponding to a position at which the element appears or disappears for the user, and the extreme vertical or horizontal position being used to determine the center of rotation of the eyes of the user during the geometrical eye parameter determining step, wherein the binocular display device comprises a left-side see-through lens and a right-side see-through lens including respective an optical component, wherein the optical components respectively include an electroactive dimmer, and wherein the active dimmer is an electrochromic device.

2. The method according to claim 1, wherein the binocular display device is configured to display images towards the two eyes of the user having both independent features and common features.

3. The method according to claim 1, wherein the subjective distortion or visibility of the perceived image relates to the subjective distortion of the perceived image.

4. The method according to claim 1, wherein the display device comprises a right and left lens through which the user sees the images displayed to the right and left eyes respectively and prior to the display image step the method comprises an image processing step during which the image to be displayed is processed to compensate the optical distortion induced by the lenses through which the user sees the images displayed.

5. The method according to claim 4, wherein during the display parameter modifying step the image to be displayed is processed until the subjective distortion of the perceived image is canceled or perceived as optimal by the user.

6. The method according to claim 4, wherein the display device comprises moveable lenses through which the user sees the images displayed and during the display parameter modifying step the lenses are moved in a plan perpendicular to the optical axis of said lenses until the subjective distortion of the perceived image is perceived as optimal by the user.

7. The method according to claim 1, wherein the image displayed to the user comprises a grid.

8. The method according to claim 1, wherein the display device comprises a moveable display pupil through which the user sees the images displayed and during the display parameter modifying step the moveable display pupil is moved in a plan perpendicular to the optical axis of the display device so as to determine the extreme vertical or horizontal positions of the display pupil, the extreme vertical or horizontal position corresponding to a position at which the element appears or disappears for the user in the perceived image, the extreme vertical or horizontal position are used to determine the center of rotation of the eyes of the user and/or diameter of the pupil of the wearer during the geometrical eye parameter determining step.

9. The method according to the claim 1, wherein the display device comprises a light-field lenses array through which the user sees the images displayed and during display parameter modifying step the image is displayed through each lenses of the light-field lenses array so as to determine the extreme vertical or horizontal position of the lenses within which the user sees the element, the extreme vertical or horizontal position being used to determine the center of rotation of the eyes of the user and/or size of the pupil of the wearer during the geometrical eye parameter determining step.

10. The method according to claim 2, wherein the subjective distortion or visibility of the perceived image relates to the subjective distortion of the perceived image.

11. The method according to claim 2, wherein the display device comprises a right and left lens through which the user sees the images displayed to the right and left eyes respectively and prior to the display image step the method comprises an image processing step during which the image to be displayed is processed to compensate the optical distortion induced by the lenses through which the user sees the images displayed.

12. The method according to claim 3, wherein the display device comprises a right and left lens through which the user sees the images displayed to the right and left eyes respectively and prior to the display image step the method comprises an image processing step during which the image to be displayed is processed to compensate the optical distortion induced by the lenses through which the user sees the images displayed.

13. The method according to claim 2, wherein the image displayed to the user comprises a grid.

14. The method according to claim 3, wherein the image displayed to the user comprises a grid.

15. The method according to claim 4, wherein the image displayed to the user comprises a grid.

16. The method according to claim 5, wherein the image displayed to the user comprises a grid.

17. The method according to claim 6, wherein the image displayed to the user comprises a grid.

18. The method of claim 8 wherein the extreme vertical or horizontal position is used to determine the diameter of the pupil of the wearer during the geometrical eye parameter determining step.

19. A system for determining an eye parameter of a user of a display device, the system comprising:

display device providing means, configured to provide to a user a binocular display device, the binocular display device being configured to display independently images towards the two eyes of the user, image display means, configured to display an image to the user when using the display device, display parameter modifying means, configured to modify at least one parameter of the display device so as to modify the distortion or visibility of the perceived image, wherein the display parameter modifying means are further configured to modify the at least one parameter until image subjective distortion or visibility of the perceived image is perceived by the user as optimal, and eye parameter determining means configured to determine an eye parameter based on the parameter of the display device, and wherein the image displayed to the user comprises an element displayed straight ahead for the user and the subjective quality of the perceived image relates to the visibility of the element in the perceived image by the user, and wherein the display device comprises a light-field lenses array through which the user sees the images displayed and during the display parameter modifying step the image is displayed through each lenses of the light-field lenses array so as to determine the extreme vertical or horizontal position of the lenses, the extreme vertical or horizontal position corresponding to a position at which the element appears or disappears for the user, and the extreme vertical or horizontal position being used to determine the center of rotation of the eyes of the user during the geometrical eye parameter determining step, wherein the binocular display device comprises a left-side see-through lens and a right-side see-through lens including respective an optical component, wherein the optical components respectively include an electroactive dimmer, and wherein the active dimmer is an electrochromic device.

* * * * *